United States Patent
Tischer (10) Patent No.: US 8,606,590 B2
(45) Date of Patent: Dec. 10, 2013

(54) METHODS, SYSTEMS, AND COMPUTER PROGRAM PRODUCTS FOR PROVIDING PERSONALIZED, JUST-IN-TIME INFORMATION SERVICES

(75) Inventor: Steven Tischer, Atlanta, GA (US)

(73) Assignee: AT&T Intellectual Property I, L.P., Atlanta, GA (US)

(*) Notice: Subject to any disclaimer, the term of this patent is extended or adjusted under 35 U.S.C. 154(b) by 2373 days.

(21) Appl. No.: 11/022,531

(22) Filed: Dec. 22, 2004

(65) Prior Publication Data

US 2006/0167718 A1    Jul. 27, 2006

(51) Int. Cl.
*G06Q 10/00* (2012.01)

(52) U.S. Cl.
USPC .................................................. 705/2; 705/3

(58) Field of Classification Search
USPC ................................................................ 705/2
See application file for complete search history.

(56) References Cited

U.S. PATENT DOCUMENTS

| | | | | |
|---|---|---|---|---|
| 5,761,204 A | * | 6/1998 | Grob et al. | 370/467 |
| 6,082,776 A | * | 7/2000 | Feinberg | 283/72 |
| 6,990,588 B1 | * | 1/2006 | Yasukura | 713/186 |
| 2002/0114764 A1 | * | 8/2002 | Berryman et al. | 424/9.1 |
| 2004/0177032 A1 | * | 9/2004 | Bradley et al. | 705/38 |
| 2006/0167718 A1 | * | 7/2006 | Tischer | 705/2 |

* cited by examiner

*Primary Examiner* — Hiep V Nguyen
(74) *Attorney, Agent, or Firm* — Cantor Colburn LLP (57) ABSTRACT

Exemplary embodiments relate to methods, systems, and computer program products for providing personalized information services. Methods include generating an instance of personalized information including time-sensitive elements, and outputting the personalized information onto a medium that is affixable to a subject with which the personalized information is associated.

22 Claims, 5 Drawing Sheets

METHODS, SYSTEMS, AND COMPUTER PROGRAM PRODUCTS FOR PROVIDING PERSONALIZED, JUST-IN-TIME INFORMATION SERVICES

BACKGROUND OF THE INVENTION

Exemplary embodiments of the invention relate generally to information technology, and more particularly, to methods, systems, and computer program products for providing personalized, just-in-time information services.

Various situations may occur which require identification and/or tracking of people or objects. For example, the elderly and the very young may not have the capacity to effectively communicate information relating to their needs (e.g., medical conditions). Mentally challenged individuals may also have difficulty communicating their needs to others. There are also a variety of conditions that may occur which cause temporary incapacitation of otherwise healthy individuals (e.g., car accident, stroke, heart attack, etc.). As with individuals, animals and/or inanimate objects may also require identification and/or tracking for various reasons (e.g., a package on route to a destination).

The ability to identify and/or track individuals at a large-scale event can be challenging. Large crowds, ambient noise, and facilities with complex navigational structures reflect just a few of the elements that may contribute to the disorientation and separation of people. In fact, many individuals avoid these types of environments due to the incumbent stress and anxiety over the possibility of losing track of a loved one.

Important information regarding an individual (e.g., medical needs) may conceivably change from day to day (e.g., a very young child who is on a short-term medicine regime) and may require that this information be conveyed in the event that the child becomes separated with a responsible adult. The information may also change depending upon the location of an event to which the individual will attend (e.g., the individual visiting relatives across the country may require that different emergency contact information be conveyed).

What is needed is a way to quickly identify and/or track individuals, animals, and objects and for providing critical information as well. This capability could be utilized to promote safety, provide instant medical information and, consequently, peace of mind for associated individuals.

SUMMARY OF THE INVENTION

Exemplary embodiments of the invention relate to methods, systems, and computer program products for providing personalized information services. Methods include generating an instance of personalized information including time-sensitive elements, and outputting the personalized information onto a medium that is affixable to a subject with which the personalized information is associated.

Exemplary embodiments further include systems for providing personalized information services. Systems include a descriptor assembly application executing on a processor. The descriptor assembly application generates an instance of personalized information including time-sensitive elements. The system also includes an output device in communication with the descriptor assembly application for outputting the personalized information onto a medium that is affixable to a subject with which the personalized information is associated.

Computer program products for providing personalized, just-in-time information services include instructions for performing a method. The method includes generating an instance of personalized information including time-sensitive elements, and outputting the personalized information onto a medium that is affixable to a subject with which the personalized information is associated.

Other systems, methods, and/or computer program products according to exemplary embodiments will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

Referring now to the drawings wherein like elements are numbered alike in the several FIGURES.

DETAILED DESCRIPTION OF EXEMPLARY EMBODIMENTS

According to exemplary embodiments, the personalized information system functions provide a means for relating personalized information, including identity information that is unique to a particular person, animal, or object, without having a-priori knowledge about the person, animal, or object. In alternative exemplary embodiments, the personalized information system may include network connectivity elements for corroborating the identification determination. The personalized information system provides just-in-time features that enable individuals to continuously convey timely, up-to-date, and situationally dependent information whenever needed. The personalized information may be applied to a substrate that is self-destructing in a manner that is commensurate with the currency of the information contained therein. This capability may be implemented utilizing, e.g., intelligent inks such as thermochromic, electrochromic, and/or photochromic materials.

Figure 1:
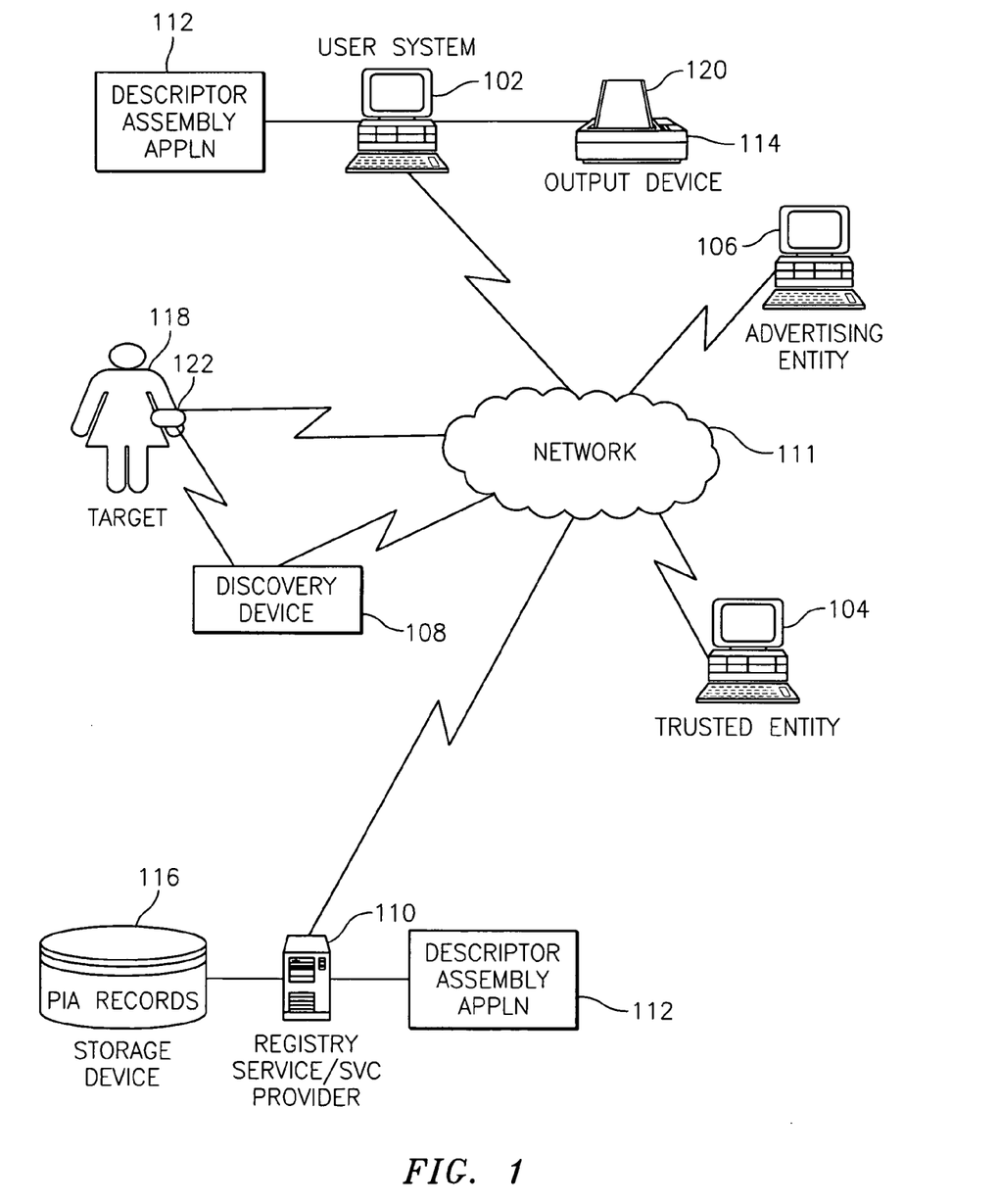
FIG. 1 is a block diagram of a system upon which the personalized information system functions may be implemented in exemplary embodiments.

Referring now to FIG. 1, a block diagram of an exemplary system for implementing the personalized information system is generally shown. The system of FIG. 1 includes a user system 102 in communication with one or more entities 104-110 over a network 111. The network 111 may be any type of communication network, including but not limited to the Internet, an intranet, extranet, local area network, cellular network, wireless network, etc. User system 102 may communicate with entities 104-110 over the network 111 utilizing one or a combination of communications technologies including, e.g., satellite or cellular technology, circuit-switched networking, and packet-switched networking, among others.

User system 102 may comprise a personal computer, e.g., desktop, laptop, portable handheld device, or similar type of processor-enabled device. In exemplary embodiments, user system 102 executes an application for implementing the information system activities. The descriptor assembly application 112 enables an operator of user system 102 to prepare and implement personalized information artifacts as will be described further herein. User system 102 may also execute a web browser and/or messaging application (e.g., email, facsimile, instant messaging). Further, user system 102 may execute a graphics application, photo-imaging application, encryption software, and other software that may be used in association with the descriptor assembly application 112 as described herein. Descriptor assembly application 112 may be a stand-alone application resident on user system 102 or may be accessible to user system 102 over a network such as network 111 via, e.g., the web browser program.

In accordance with exemplary embodiments, user system 102 is coupled to an output device 114 via, e.g., a universal serial bus (USB) cable, over a wireless network, or other suitable technology. Output device 114 may be a general-purpose printing device or other suitable device, e.g., a 3D lithographic outputter.

Trusted entity 104 refers to a computer device that is operated by an authorized individual or authority (e.g., police, fire department, emergency room, government agency, etc.). Trusted entity 104 may receive identification information from a variety of users of the information system and may retain and manage records of this information, if desired. Advertising entity 106 refers to a third-party source of information that may be provided on the personalized information artifacts generated by the descriptor assembly application 112. Trusted entity 104 and advertising entity 106 may each comprise personal computers or networked computers that communicate with user system 102 and/or a registry service system 110 over network 111.

In alternative exemplary embodiments, registry service system 110 provides personalized information management services to individuals or businesses such as user system 102, trusted entity 104, and advertising entity 106. Registry service system 110 may execute the descriptor assembly application 112 and provide authorized entities such as user system 102 with access to the descriptor assembly application 112 as described above. In exemplary embodiments, registry service system 110 may be implemented via a server that is in communication with a storage device 116. Storage device 116 stores data, records, etc., such as personalized information artifact records as described further in the diagram of FIG. 4. The server of registry service system 110 may comprise any suitable high-speed microprocessor capable of handling the volume of activities provided by the features and functions of the descriptor assembly application 112. The server may be accessed over the communications network 111 and may further include a security feature or firewall (not shown) in order to protect the integrity of the data stored within the server and storage device 116.

Registry service system 110 may be included in a venue that either hosts an event (e.g., concert, amusement park, festival) or in a business that desires to provide personalized information services as a value-added offering (e.g., medical facility, photo developer enterprise, etc.). Alternatively, registry service system 110 may be used in a private organization that provides personalized information services to its members or may be a commercial enterprise such as a network service provider (e.g., Internet Service Provider).

The descriptor assembly application 112 enables user system 102 to create and print personalized information artifacts, a sample of which is shown generally in FIG. 1 affixed to a subject 118. A user may configure the artifacts in a variety of ways and print them out onto a medium 120 shown with respect to output device 114. The medium 120 may be any type of substrate capable of being affixed to a surface. The personalized information provided on these artifacts is specific to subject 118, which may be, e.g., a human, animal, or object. For illustrative purposes, subject 118 as shown in FIG. 1 is a human with a personalized information artifact 122 affixed to the arm.

The information provided on personalized information artifact 122 may be encoded using various encoding techniques, such as bar coding, glyphs, etc., in order to prevent unauthorized entities or individuals from acquiring protected information. A scanning device may be used to retrieve the encoded information. As shown in the system diagram of FIG. 1, discovery device 108 scans the personalized information artifact 122 and transmits the information over network 111 to one or more of user system 102, trusted entity 104, and registry service 110.

Figure 2:
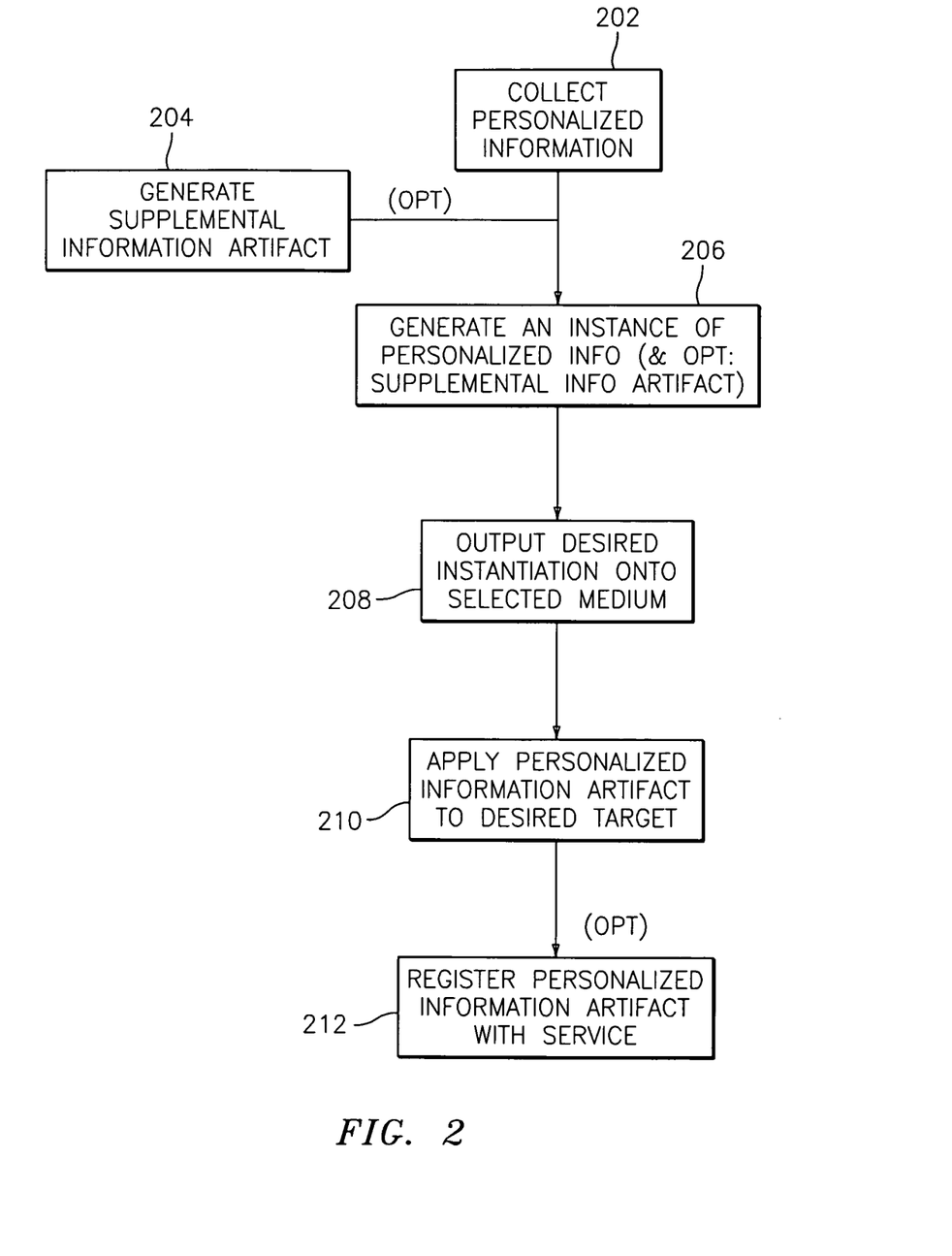
FIG. 2 is a flow diagram describing a process for implementing the personalized information system functions in exemplary embodiments.

Turning now to the flow diagram of FIG. 2, an exemplary process for implementing the personalized information system functions will now be described. At step 202, personalized information data is collected. Elements of personal information suitable for inclusion in a personalized information artifact 122 may include subject identification information such as name, address (e.g., residential, vCard, etc), gender, and age. Graphical information such as a digitized photograph of the subject 118 may also be utilized. In addition, medical information such as a current drug list (including medications recently ingested by the subject 118) may be included. If the subject is an object such as a package, the information provided may include handling instructions, routing instructions, special care instructions (e.g., fragility, temperature exposure limitations, toxicity, etc.).

Medical information may be dynamically generated via a household media center associated with the subject (e.g., user system 102). Persistent conditions such as diabetes, blindness, and mental retardation may be included in the personalized information artifact 122. Unique information sets such as blood type and family history may be included, as well as disambiguous markers such as security keys, social security numbers, etc. Using scanning devices (e.g., discovery device 108) at the time of generation of the personalized information artifacts 122, other information sets may be leveraged and used to assist in disambiguating the content of the personalized information artifact 122. For example, a driver's license photo may be scanned and incorporated into the personalized information artifact 122. Alternatively, information gathered automatically via other ID systems such as Radio Frequency Identification (RFID) to collect current proximity information may be utilized in identifying and tracking elements.

Optionally, at step 204, a supplemental information artifact is generated. For example, a service or entity (e.g., registry service system 110) providing personalized information services may produce quantities of personalized information artifacts, whereby a portion of each include pre-printed information such as advertising received from advertising entity 106, and/or community group information. For example, pre-printed information may include the name of the service provider, a current date, network elements, etc. Network elements are described further in FIGS. 2 and 3. Community group information may assist in identifying groups of individuals or subjects that belong to a designated community (e.g., club organization, classroom students, travel tour members, etc.). Community group information may alternatively designate the service provider (e.g., entity 110) that is offering the personalized information services.

The descriptor assembly application 112 generates an instance of the personalized information data and, if used, the supplemental information artifact at step 206. This may be accomplished either remotely (e.g., mailing service that enables users to create a 'use once' sticker for a package) or may be accomplished locally (e.g., a computer or handheld device that outputs a sticker). The descriptor assembly application 112 also formats the information set's constituent parts in order to accommodate a particular need. For example, the format may be a simple photograph and adjacent emergency service number, or a complex formatting that requires a standardized structure for use with other system, such as 'health bracelets' or other emergency services. Additionally, information encryption may be utilized as desired in order to output any required information, such as a distributed glyph creation or other encryption. Applying these types of technologies to a personalized information artifact 122 may be useful in enabling the artifact 122 to withstand some degree of degradation while preserving the information contained therein.

Figure 5:
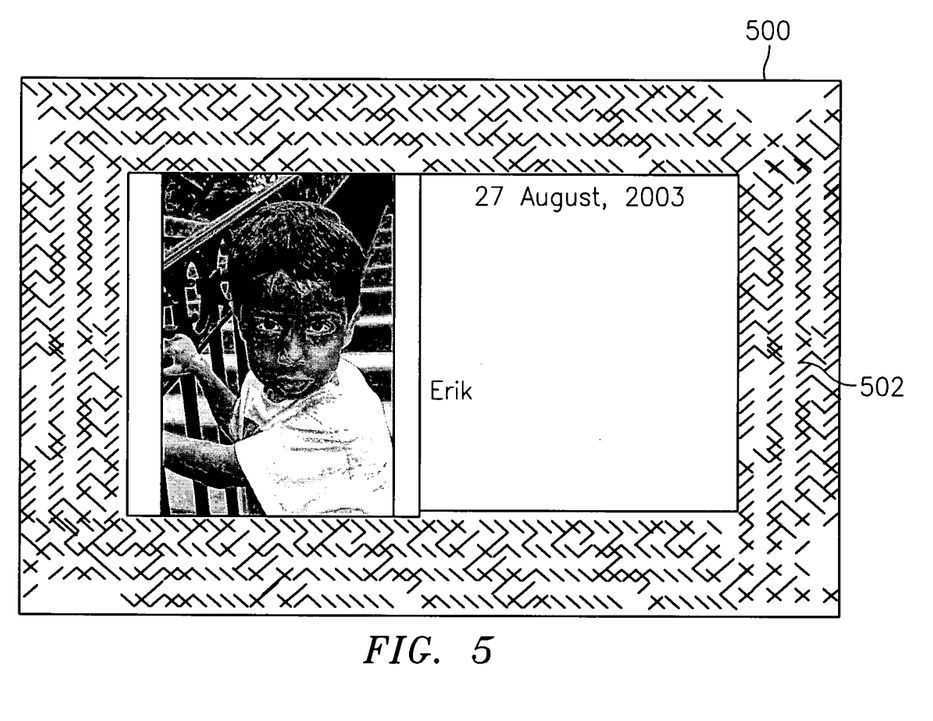
FIG. 5 is a sample personalized information artifact generated via the personalized information system in alternative exemplary embodiments.
Figure 6:
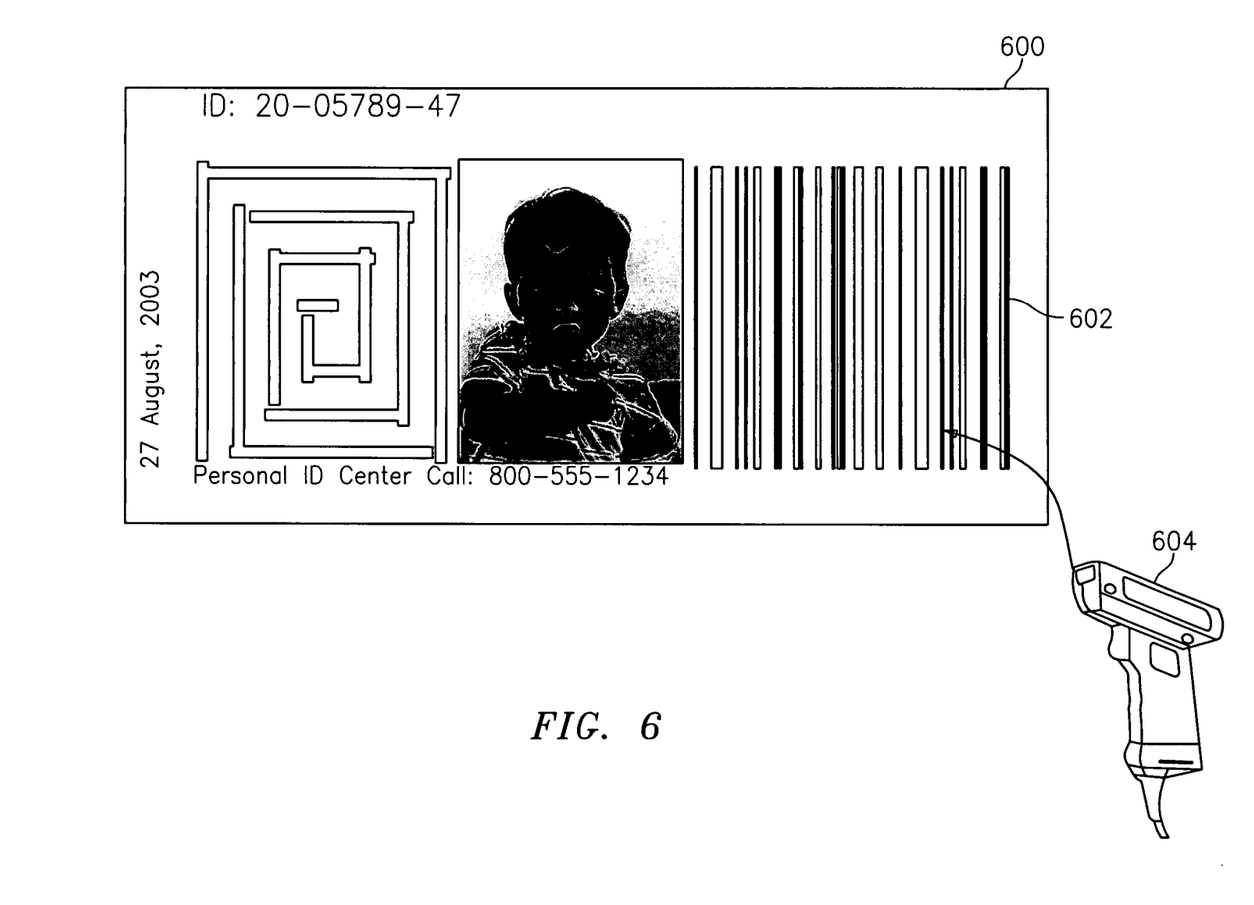
FIG. 6 is a sample personalized information artifact generated via the personalized information system in further exemplary embodiments.

At step 208, the instantiation is outputted to a selected medium. This may be accomplished by printing or outputting the information onto a stick-on substrate, similar to the process performed with band-aids in a typical production process. Alternatively, this may be accomplished by printing or outputting the information set onto a temporary tattoo medium. In yet further embodiments, this may be performed by outputting the information set into an electronic facsimile for transmission to the management service for allowing later querying and identification matching. Sample representations of a personalized information artifact are shown in FIGS. 3, 5, and 6.

The personalized information artifact is applied to the desired target at step 210. This may be applied on the skin, clothing, or other object surface.

Optionally, the personalized information artifact may be registered with a service at step 212. The service may be utilized for responding to any queries concerning the personalized information artifact. For example, if the personalized information artifact includes network elements, the information contained therein may be actively transmitted over a network (e.g., network 111) to the registry service system or may be passively transmitted via, e.g., discovery device 108 over network 111.

Figure 3:
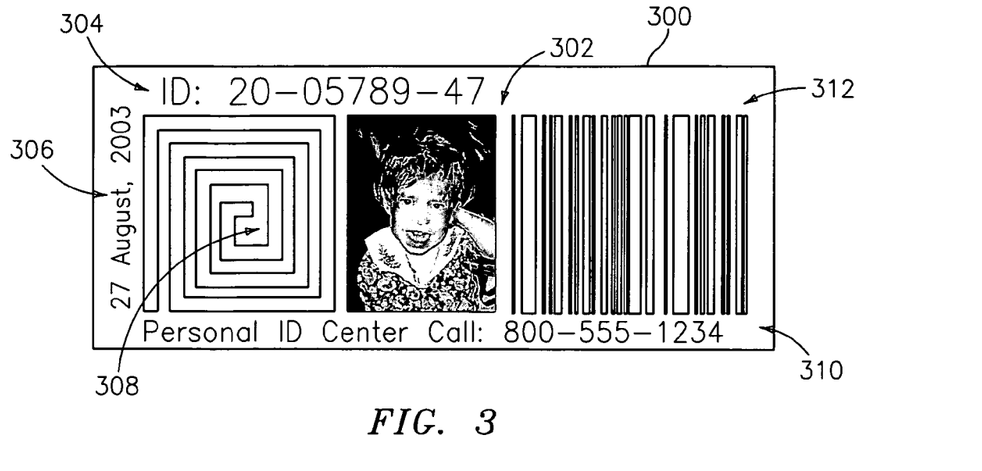
FIG. 3 is a sample personalized information artifact generated via the personalized information system in exemplary embodiments.

A sample representation of a personalized information artifact is shown in FIG. 3. Personalized information artifact 300 includes a photo 302 of the artifact subject for aiding in identifying the subject if needed. Personalized information artifact 300 also includes a unique identification 304 that is uniquely assigned to the artifact 300. Current information may be presented such as the date 306. Other symbology 308 is shown in the artifact 300 and may include network elements such as an antenna, battery, and memory that are capable of actively transmitting information concerning the subject over a network. Current technology for printing antennae, batteries, and memory as understood by those skilled in the art may be used for printing the symbology 308. Contact information 310 may also be presented on the artifact 300 for informing an entity (e.g., trusted entity 104) of a means for contacting a relevant source. Finally, artifact 300 includes encoded information (i.e., personalized information that has been encoded) 312. For illustrative purposes the information is encoded utilizing bar coding technology.

Figure 4:
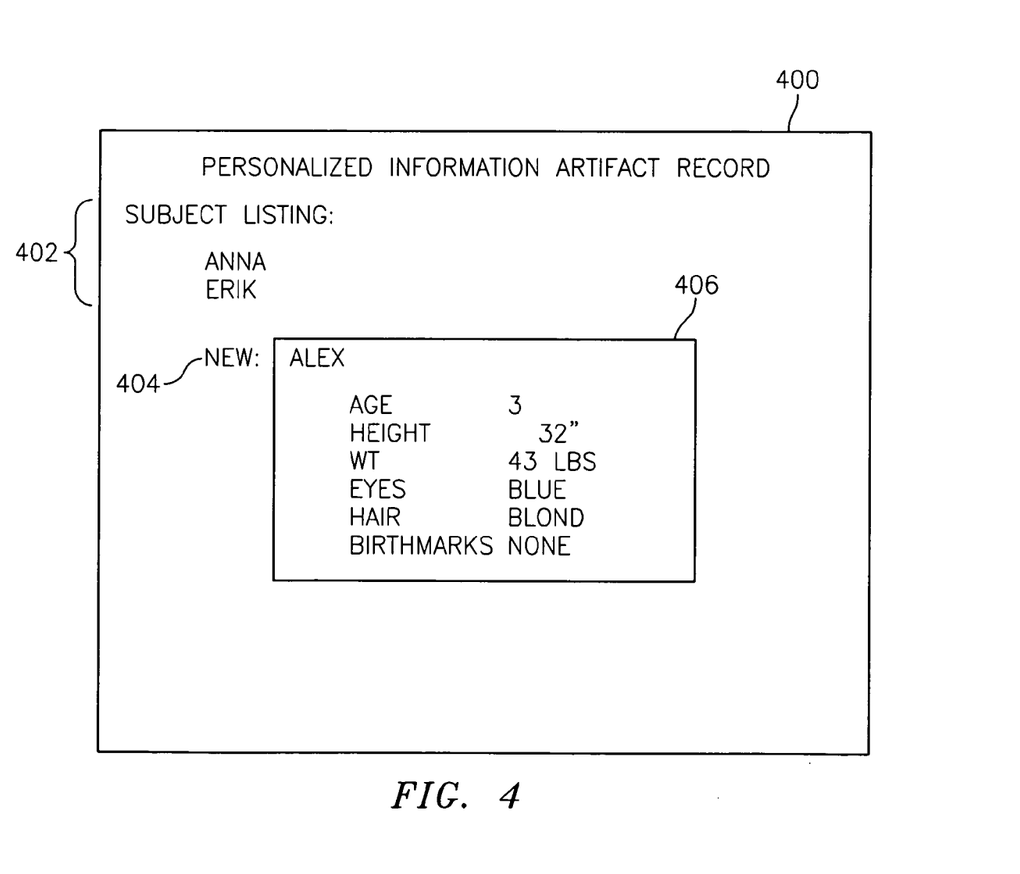
FIG. 4 is an information artifact record generated via the personalized information system in exemplary embodiments.

If a registry service (e.g., registry service system 110) is utilized, much of the information described in FIG. 3 may be stored in an information artifact record generated via the descriptor assembly application 112, a sample of which is shown in FIG. 4. Information artifact record 400 may store information for each subject associated with a service recipient (e.g., a family). For example, record 400 displays a listing 402 of two subjects, Anna and Erik. A service recipient (or registry service system individual) may add a new subject 404 to the listing, whereby a subwindow 406 is presented for entering information relating to the new subject. As shown in subwindow 406, a new subject record is created for Alex, along with desired personalized information.

As described above, various types of encoding means may be utilized in protecting personalized information presented on an artifact. A sample representation of a personalized information artifact utilizing glyph technology is shown generally in FIG. 5. Personalized information artifact 500 includes glyph encoding 502 presented in a border-like fashion around the perimeter of the artifact 500. A discovery device may be utilized for decoding the information as desired. For example, a trusted authority such as entity 104 may possess the required devices for decoding the glyph information.

Turning now to FIG. 6, a sample personalized information artifact 600 is generally shown. Personalized information artifact 600 includes information 602 that is encoded utilizing bar coding technology. A scanning device such as a bar code scanner 604 retrieves the encoded data from the artifact 600 and translates the information into a readable form.

In alternative exemplary embodiments, the personalized information artifact may be generated using a RAID-like array where information is distributed over a medium and is reconstructable even where parts of the medium are missing. For example, the artifact may be designed so that designated information elements are assigned a specific location on the artifact. The existing (non-worn) information elements provide some of the information needed to reconstruct the missing information (e.g., using a checksum along with the existing information elements to inferentially determine the missing elements).

As indicated above, the personalized information system functions provide a means for relating personalized information, including identity information that is unique to a particular person, animal, or object, without having a-priori knowledge about the person, animal, or object. The personalized information system provides just-in-time features that enable individuals to continuously convey timely, up-to-date, and situationally dependent information whenever needed. The personalized information may be applied to a substrate that is self-destructing in a manner that is commensurate with the currency of the information contained therein.

As described above, embodiments may be in the form of computer-implemented processes and apparatuses for practicing those processes. In exemplary embodiments, the invention is embodied in computer program code executed by one or more network elements. Embodiments include computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Embodiments include computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the claims.

What is claimed is:

1. A method for providing personalized information services, comprising:
    generating, via an application executing on a computer processor device, an instance of personalized information including time-sensitive elements; and
    outputting, via the application, the personalized information onto a medium comprising at least one of a bandage and a temporary tattoo, the medium affixable to a subject with which the personalized information is associated;
    wherein the subject is a human and at least a portion of personalized information output to the medium self-destructs over a time period that is commensurate with the time-sensitive elements.

2. The method of claim 1, wherein the outputting includes incorporating communication elements onto the medium and transmitting at least a portion of the personalized information over a network via the communication elements.

3. The method of claim 1, wherein the outputting further comprises:
    encoding at least a portion of the personalized information using an encoding means that prevents unauthorized entities or individuals from acquiring the personalized information from the medium.

4. The method of claim 1, wherein the personalized information includes at least one of:
    subject identification information comprising at least one of:
        a subject name;
        a subject age;
        a subject description;
        a subject gender; and
        a subject address;
    a health condition associated with the subject; and
    emergency contact information relating to the subject.

5. The method of claim 1, wherein the time-sensitive elements include at least one of:
    a temporary medical condition associated with the subject;
    medical care instructions;
    medications recently ingested; and
    a current date or time.

6. The method of claim 1, wherein the time-sensitive elements include a temporary location frequented by the subject.

7. The method of claim 1, further comprising:
    reconstructing destroyed personalized information.

8. The method of claim 1, wherein the outputting includes outputting the personal information onto a medium having pre-printed information.

9. The method of claim 8, wherein the pre-printed information includes advertising.

10. A system for providing personalized information services, comprising:
    a computer processor device;
    a descriptor assembly application executing on the computer processor device, the descriptor assembly application generating an instance of personalized information including time-sensitive elements; and
    an output device in communication with the descriptor assembly application, the output device outputting the personalized information onto a medium that is affixable to a subject with which the personalized information is associated;
    wherein at least a portion of personalized information output to the medium self-destructs over a time period that is commensurate with the time-sensitive elements; and
    wherein self-destructing elements of the medium are imprinted using intelligent ink comprising at least one of:
    thermochromic properties;
    electrochromic properties; and
    photochromic ink properties.

11. The system of claim 10, wherein the output device outputs communication elements onto the medium and transmits at least a portion of the personalized information over a network via the communication elements.

12. The system of claim 10, wherein the outputting includes:
    encoding at least a portion of the personalized information using an encoding means that prevents unauthorized entities or individuals from acquiring the personalized information from the medium.

13. The system of claim 10, wherein the personalized information includes at least one of:
    subject identification information comprising at least one of:
        a subject name;
        a subject age;
        a subject description;
        a subject gender; and
        a subject address;
    a health condition associated with the subject; and
    emergency contact information relating to the subject.

14. The system of claim 10, wherein the time-sensitive elements include at least one of a temporary medical condition associated with the subject;
    medical care instructions;
    medications recently ingested;
    a current date or time; and
    a temporary location frequented by the subject.

15. The system of claim 10, wherein the medium is one of a bandage and a temporary tattoo, and the subject is a human.

16. The system of claim 10, wherein the descriptor assembly application further performs:
    reconstructing destroyed personalized information.

17. A computer program product for providing personalized information services, the computer program product including a computer storage medium having instructions embodied thereon, which when executed by a computer processor, cause the computer processor to perform the steps of:
    generating an instance of personalized information including time-sensitive elements, the instance generated using an array where the personalized information, once output, are assigned a specific location on a medium; and outputting the personalized information onto the medium, the medium affixable to a subject with which the personalized information is associated;

reconstructing destroyed personalized information using a checksum along with personalized information on the medium that is not destroyed, and inferentially reconstructing the destroyed personalized information;

wherein at least a portion of personalized information output to the medium self-destructs over a time period that is commensurate with the time-sensitive elements.

18. The computer program product of claim 17, wherein the outputting includes incorporating communication elements onto the medium and transmitting at least a portion of the personalized information over a network via the communication elements.

19. The computer program product of claim 17, wherein the outputting further comprises:

encoding at least a portion of the personalized information using an encoding means that prevents unauthorized entities or individuals from acquiring the personalized information from the medium.

20. The computer program product of claim 17, wherein the personalized information includes at least one of:

subject identification information comprising at least one of:
a subject name;
a subject age;
a subject description;
a subject gender; and
a subject address;

a health condition associated with the subject; and emergency contact information relating to the subject.

21. The computer program product of claim 17, wherein the time-sensitive elements include at least one of:

a temporary medical condition associated with the subject;
medical care instructions;
medications recently ingested;
a current date or time; and
a temporary location frequented by the subject.

22. The computer program product of claim 17, wherein the medium is one of a bandage and a temporary tattoo, and the subject is a human.

* * * * *